United States Patent [19]

Nagano

[11] Patent Number: 5,418,829
[45] Date of Patent: May 23, 1995

[54] METHOD FOR DETERMINING UNKNOWN STRUCTURE OF CRYSTAL

[75] Inventor: Seido Nagano, Tokyo, Japan

[73] Assignee: Nec Corporation, Tokyo, Japan

[21] Appl. No.: 260,454

[22] Filed: Jun. 14, 1994

[30] Foreign Application Priority Data

Jul. 1, 1993 [JP] Japan .................. 5-163032

[51] Int. Cl.⁶ .......................... G01N 23/223
[52] U.S. Cl. ........................ 378/86; 378/73; 250/307
[58] Field of Search ............ 378/70, 71, 72, 73, 378/74, 75, 76, 77, 79, 81, 86, 88; 250/251, 307; 356/445, 446, 448

[56] References Cited

U.S. PATENT DOCUMENTS

| | | | |
|---|---|---|---|
| 4,074,132 | 2/1978 | Ladell et al. | 378/73 |
| 4,553,030 | 11/1985 | Tokiwai et al. | 250/307 |
| 4,788,702 | 11/1988 | Howe et al. | 378/71 X |
| 5,235,523 | 8/1993 | Karen et al. | 378/73 X |

FOREIGN PATENT DOCUMENTS

8808530 11/1988 WIPO ..................... 378/86

OTHER PUBLICATIONS

By S. Nagano, "Theory of reflection high-energy electron diffraction", Oct. 1990, vol. 42, No. 12, The American Physical Society, pp. 7363-7369.

*Primary Examiner*—David P. Porta
*Attorney, Agent, or Firm*—Young & Thompson

[57] ABSTRACT

The method for determining unknown structure of a solid by means of corpuscular beams or electromagnetic waves, includes the steps of radiating first incident waves to the solid to thereby obtain first scattering waves, radiating second incident waves to the solid in the direction opposite to the direction in which the first scattering waves had travelled, to thereby obtain second scattering waves, and measuring the intensity of the second scattering waves and the direction in which the second scattering waves had travelled.

12 Claims, 1 Drawing Sheet

METHOD FOR DETERMINING UNKNOWN STRUCTURE OF CRYSTAL

BACKGROUND OF THE INVENTION

1. Field of the Invention

The invention relates to a method for determining unknown structure of a solid, and more particularly to such a method by measuring scattering waves of incident corpuscular beams or electromagnetic waves radiated to a solid having unknown structure.

2. Description of the Related Art

For determining unknown structure of a solid, the trial and error process and Fourier process had conventionally been used. In the trial and error process, the intensity of diffraction is first measured from scattering of incident X-ray beams or neutron beams, and then compared to theoretical intensity of diffraction of expected crystal structure. This step is repeated until the measured intensity is coincident with the theoretical intensity. In Fourier process, the location of atoms are determined by Fourier transformation of diffraction intensity of a plurality of diffraction spots. These processes determine crystal structure of bulk materials in particular, but cannot avoid to have ambiguity or obscurity in determining a structure of a soil d because it is necessary in the trial and error process to assume in advance a crystal structure, and because Fourier process has to select the finite number of diffraction spots.

There has been used another method for determination of unknown structure of a solid. In this method, electrons are first radiated over a surface of the crystal structure or a thin film, and then the intensity of scattering waves and the direction in which the scattering waves travel led are measured. The structure of the surface or thin film can be determined by analyzing the measurements. In particular, the low-energy electron diffraction (LEED) and the reflection high-energy electron diffraction (RHEED) are well known. As is known in the art, in LEED process, electrons having energy in the range of 20-500 eV are radiated perpendicularly to a surface of a crystal structure, and then reflected electron waves are obtained. These reflected electron waves represent data about the structure of several atom layers disposed slightly below the surface. In RHEED process, electrons having energy of 20-50 KeV are radiated quite close to a surface of an object, and then there can be obtained reflected waves representing data about the structure of atom layers disposed slightly below the surface.

In these processes for analyzing an unknown structure of a solid, energy of incident electrons are varied to measure the intensity of diffraction spots of reflected electrons. More specifically, so-called I–V curve which is a function of energy of the incident electrons is obtained by virtue of data represented by the reflected electrons, and is observed. Then, a structure of crystal is assumed, scattering intensity of corresponding electrons is calculated, and finally the assumed structure is compared to the calculation. This procedure is repeated until the assumed structure is coincident with the calculation. It often takes more than a year to analyze a structure in these processes. If an object has an increased number of atoms, it is almost impossible to exactly determine a structure of the object. In addition, incident energy is varied in these processes to avoid obscurity in determining the structure, however, scattering conditions are also varied together with the incident energy, which may prevent determination of unique structure.

SUMMARY OF THE INVENTION

When a new solid is to be developed, it is quite important to determine the structure of the solid exactly and rapidly. It is an object of the present invention to provide a method for determining the structure of a solid exactly and swiftly, involving multiple scattering effect which plays an important role in determination of the structure of a solid, and avoiding ambiguity and complexity involved in a conventional method such as the above mentioned trial and error method.

The inventor has made researches so far into determination of unknown structure of a solid in order to shorten time for such determination and also make it possible to automatically accomplish such determination. As a result of the inventor's researches, the inventor has come across a discovery that the aforementioned problems of conventional processes can be entirely overcome by a newly found method, in which incident waves are first radiated to an object to thereby obtain first scattering waves, and then second incident waves are radiated to the object in the direction opposite to the direction in which the first scattering waves had passed to thereby obtain second scattering waves, and finally the direction and intensity of the second scattering waves are measured. The inventor had established theory of reflection high-energy electron diffraction exactly involving multiple scattering, and had reported the theory in PHYSICAL REVIEW B, VOLUME 42, NUMBER 12 OCTOBER, 1990, pages 7363-7369. In this report, it was made apparent that the relationships between all incident waves and scattering waves are related to each other through a matrix containing therein characteristics of an object, if energy of the incident waves are fixed or if monochrome waves having constant wavelength are to be used. It should be noted that such a matrix corresponds to a matrix R or T in the above mentioned report. It has been also found that conventional processes such as the aforementioned ones could provide data corresponding to only a first column or a first row of the matrix R or T, It is absolutely necessary to obtain data corresponding to all of elements of the matrix R or T in order to exactly determine an unknown structure of a solid without using the aforementioned trial and error procedure.

The inventor had continued to make researches into this matter and studied various aspects of multiple scattering, and had at last come across quite an important discovery. Namely, it had been found that if incident waves energy of which is set to be fixed is radiated to an object in the direction corresponding to the direction for the first radiated vector added to a reciprocal-lattice vector, the intensity of scattering waves represent data about a column vector or a row vector corresponding to the intensity of scattering waves. In general, each atom present in a crystal has three unknowns represented with x, y and z coordinates and hence there are 3n unknowns for n number of atoms. Accordingly, it is necessary to have 3n data in order to determine where n number of atoms are located. In other words, it is required to have at least 3n number of independent equations which are functions of the locations of the n number of atoms. Since the above mentioned matrix R or T has more than 3n number of data relating to location of atoms, the measurement accomplished using a set of incident waves which are different from each other by a reciprocal-lattice vector provides at least 3n number of data independent of each other. As a result, it is possible to determine the exact location of atoms, taking the multiple scattering effect into consideration.

Then, a next problem is how a reciprocal-lattice of unknown crystal structure can be determined in advance. Namely, the reciprocal-lattice cannot be determined unless the crystal structure is determined. To this end, the inventor has developed quite a new process. The inventor has found the fact that incident waves radiated to an object has a specific relationship with scattering waves thereof including reflected waves and transmitted waves. More specifically, the inventor has found that the scattering waves are different from the incident waves by a reciprocal-lattice vector. Accordingly, the aforementioned problems can be resolved by the process in which first incident waves are radiated over an object and first scattering waves thereof are observed, and then second incident waves are radiated over an object in the direction opposite to the direction in which the first scattering waves traveled and second scattering waves thereof are observed in terms of the intensity and direction thereof.

The solid structure analysis procedure using the aforementioned process can be applied to an electron diffraction process and other structural analyses using electromagnetic waves such as X-ray and corpuscular beams such as neutron. Thus, the process in accordance with the invention can be widely used, and is suitable in particular for structural analysis of a lot of atoms. Data represented by the scattering waves provide a group of equations having a function of location of atoms, and hence it is possible to use a calculator for solving the equations automatically as an issue of multi-dimensional minimization.

Specifically, the present invention provides a method for determining unknown structure of a solid by means of corpuscular beams or electromagnetic waves. This method includes the steps of radiating first monochrome beams of one of corpuscular beams and electromagnetic waves as incident waves to a solid having unknown structure to thereby obtain first scattering waves, radiating second monochrome beams having the same wavelength as that of the first monochrome beams to the solid in the direction opposite to the direction in which the first scattering waves had travelled, to thereby obtain second scattering waves, and measuring the intensity of the second scattering waves and the direction in which the second scattering waves had travelled.

In a preferred embodiment, the scattering waves include transmitted waves and reflected waves.

In another preferred embodiment, the step of measuring is accomplished by means of a combination of an optical fiber and a photomultiplier.

In still another preferred embodiment, the first monochrome beams are radiated to the solid from thereabove.

In yet another preferred embodiment, the first monochrome beams are radiated to the solid from therebelow.

In still yet another preferred embodiment, the solid has crystal structure.

The invention further provides another method for determining unknown structure of a solid by means of corpuscular beams or electromagnetic waves. The method includes the steps of radiating first monochrome beams of one of corpuscular beams and electromagnetic waves as incident waves into a solid having unknown structure to thereby obtain first scattering waves, radiating second monochrome beams having the same wavelength as that of the first monochrome beams into the solid in the direction opposite to the direction in which the first scattering waves had travelled, to thereby obtain second scattering waves, measuring the intensity of the second scattering waves and the direction in which the second scattering waves had travelled, and solving a group of equations having a function of location of atoms as an issue of multi-dimensional minimization, the group of equations being constituted of the data represented by the second scattering waves.

The invention also provides a method for determining unknown structure of a solid, including the steps of radiating first incident waves to a solid having unknown structure to thereby obtain first scattering waves, radiating second incident waves to the solid in the direction opposite to the direction in which the first scattering waves had travelled, to thereby obtain second scattering waves, and measuring the intensity of the second scattering waves and the direction in which the second scattering waves had travelled.

In a preferred embodiment, the second incident waves have the same wavelength as that of the first scattering waves.

In another preferred embodiment, the both first and second incident waves are monochrome waves.

The invention further provides a method for determining unknown structure of a solid, including the steps of radiating first incident waves to a solid having unknown structure to thereby obtain first scattering waves, radiating second incident waves to the solid in the direction opposite to the direction in which the first scattering waves had travelled, to thereby obtain second scattering waves; measuring the intensity of the second scattering waves and the direction in which the second scattering waves had travelled, and solving a group of equations having a function of location of atoms as an issue of minimization in the 3n-dimensional functional space, the group of equations being constituted of the data represented by the second scattering waves.

The advantages obtained by the aforementioned present invention will be described hereinbelow.

The conventional structural analysis process has used only a single scattering. In addition, the algorithm for determination of a structure is likely to include obscurity generated due to trial and error. However, the present invention provides an exact and swift method including no obscurity and further capable of being automated, for electron diffraction in which multiple scattering plays an important role, as well as structural analysis using diffraction phenomena.

The above and other objects and advantageous features of the present invention will be made apparent from the following description made with reference to the accompanying drawings, in which like reference characters designate the same of similar parts throughout the drawings.

DESCRIPTION OF THE PREFERRED EMBODIMENTS

A preferred embodiment in accordance with the invention will be explained hereinbelow with reference to drawings.

Figure 1A:
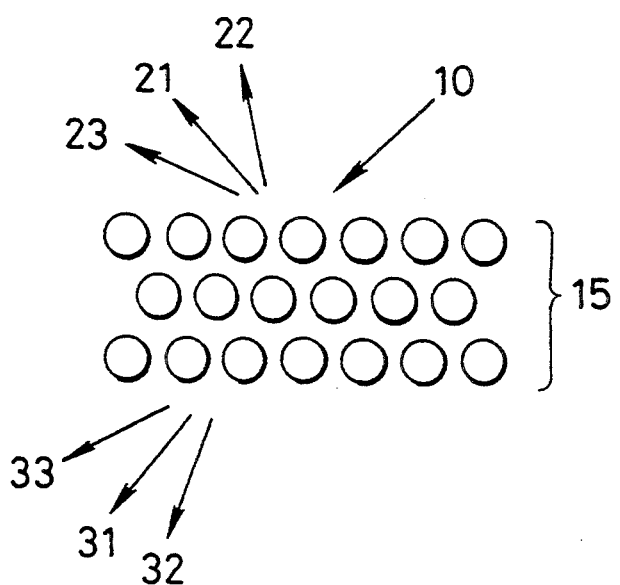
FIG. 1A is a schematic view illustrating first incident wave and first scattering waves.

Hereinbelow is shown an example of determination of unknown crystal structure. As illustrated in FIG. 1A, an incident wave 10 is first radiated to a solid 15 having unknown structure. Then, reflected waves 21, 22 and 23 and/or transmitted waves 31, 32 and 33 are generated. It should be noted that these waves 21–23 and 31–33 represent data indicating the structure of the solid 15. Then, second incident wave 40 for determination of the unknown structure of the solid 15 is identified to be radiated to the solid 15 in the direction opposite to the direction in which the scattering waves 21–23 or 31–3 3 had advanced. Thus, a set of two dimensional reciprocal-lattice vectors can be determined for analysis of the unknown structure of the solid 15.

Figure 1B:
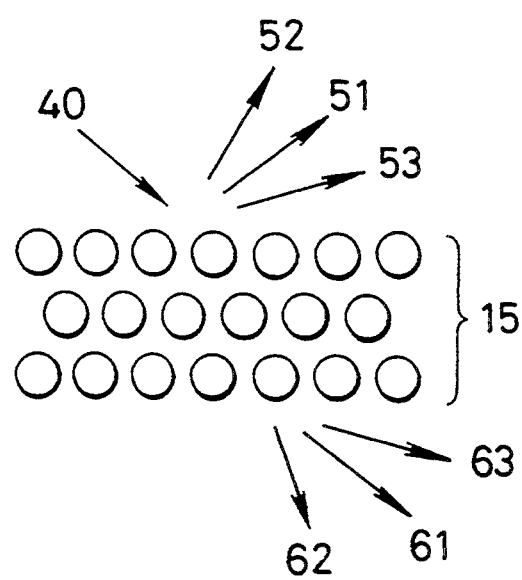
FIG. 1B is a schematic view illustrating second incident wave and second scattering waves including reflected waves and transmitted waves.

Next, as illustrated in FIG. 1B, the thus identified second incident wave 40 is radiated to thereby obtain scattering waves including reflected waves 51, 52 and 53 and transmitted waves 61, 62 and 63. The intensity of each scattering waves 51–53 and 61–63 is measured. In measurement, it is preferable to use a combination of an optical fiber and a photomultiplier on a fluorescent screen. If a unit lattice includes n particles, there are 3n unknowns. Thus, the determination of unknown structure of a solid is equivalent to an issue of minimization in the 3n-dimensional functional space. A computer program such as Powell process is well known for solving an issue of minimization in the 3n-dimensional functional space. In order to solve the issue, a series of measurements such as reflectance or transmittance are input data to the above mentioned computer program, and further reflectance or transmittance set forth in the foregoing report reported by the inventor are also input data to the program as a function of location of atoms, and finally an optimum resolution is calculated for minimizing a difference between the two inputs.

For verifying the profitability of the present invention, hereinbelow is explained an example in which electrons are radiated to a surface (100) of an ideal silicon monocrystal in a direction [110], and the structure of the monocrystal is determined by virtue of scattering of reflected high-energy electrons. Ideal crystals of silicon have a diamond shaped structure, and include eight atoms in a unit cell. There assumes a "scattered silicon crystal" having a unit cell in which locations of seven silicon atoms other than a silicon atom located at the original (000) are randomly displaced by 5% from ideal locations thereof in three dimensional fashion. Then, electrons having 20 KeV energy are radiated to the "scattered silicon crystal" in the approximately [110] direction. As a result, a lot of reflected electrons can be theoretically obtained. Then, electrons are radiated as incident beams in the directions in which most through sixth most intensive reflection had advanced, and scattering waves of high-energy electrons are measured. Among them are selected six scattering waves independent from each other and each associated with each incident beams. The reflectance of the thus selected six scattering waves are theoretically calculated in accordance with the above mentioned report. Thus, 36 data representing scattering intensity and independent from each other can be obtained. As a start structure or an initial value, there is assumed a structure in which locations of silicon atoms are displaced from ideal locations. In the embodiment, a structure is assumed in which locations of silicon atoms are randomly displaced by 20%. Then, locations of silicon atoms for providing best solution of 36 reflection intensities are calculated from the start structure by utilizing Powell process, based on the above mentioned 36 data relating to scattering intensity. As a result, the locations of the seven silicon atoms randomly displaced by 5% can be obtained with four figures accuracy by repeating calculations five times. Repeating calculations more than eight times can provide more than five figures accuracy.

Thus, it can be found that the structural analysis process in accordance with the present invention is effective to a solid having quite complex scattering structure such as the structure exampled in the above mentioned embodiment. In conventional processes, if an assumed structure is not sufficiently coincident with measurements, another assumed structure is compared to measurements until they are sufficiently coincident with each other. Accordingly, it is impossible in conventional processes to analyze quite complex scattering structure such as the embodiment. Thus, it could not be avoided in conventional processes to treat random displacement by 5% of atoms' locations as average ambiguity of atoms' locations generated due to thermal oscillation.

As explained so far, the structural analysis in accordance with the invention provides a method for simply determining an unknown structure of a solid including a mass of atoms, based on intensity data represented by specifically selected scattering waves. In determination, it is possible to use existing computer programs such as Powell process for calculating an optimum resolution for 3n dimensional unknowns. In addition, it is obvious that the present invention can be systemized as an automated structural analyzer by computerizing a combination of a beam source for providing beams such as electron and X-ray, and a diffraction apparatus having multi-axial goniometers in a sample holder.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A method for determining unknown structure of a solid by means of corpuscular beams or electromagnetic waves, said method comprising the steps of:

radiating first monochrome beams of one of corpuscular beams and electromagnetic waves as incident waves to a solid having unknown structure to thereby obtain first scattering waves;

radiating second monochrome beams having the same wavelength as that of said first monochrome beams to said solid in the direction opposite to the direction in which said first scattering waves had travelled, to thereby obtain second scattering waves; and measuring the intensity of said second scattering waves and the direction in which said second scattering waves had travelled.

2. A method in accordance with claim 1 wherein said scattering waves include transmitted waves and reflected waves.

3. A method in accordance with claim 1 wherein said step of measuring is accomplished by means of a combination of an optical fiber and a photomultiplier.

4. A method in accordance with claim 1 wherein said first monochrome beams are radiated to said solid from above said solid.

5. A method in accordance with claim 1 wherein said first monochrome beams are radiated to said solid from below said solid.

6. A method in accordance with claim 1 wherein said solid has crystal structure.

7. A method for determining unknown structure of a solid by means of corpuscular beams or electromagnetic waves, said method comprising the steps of:
- radiating first monochrome beams of one of corpuscular beams and electromagnetic waves as incident waves into a solid having unknown structure to thereby obtain first scattering waves;
- radiating second monochrome beams having the same wavelength as that of said first monochrome beams into said solid in the direction opposite to the direction in which said first scattering waves had travelled, to thereby obtain second scattering waves;
- measuring the intensity of said second scattering waves and the direction in which said second scattering waves had travelled; and
- solving a group of equations having a function of location of atoms as an issue of minimization in the 3n-dimensional functional space, said group of equations being constituted of the data represented by said second scattering waves.

8. A method in accordance with claim 5 wherein said scattering waves include transmitted waves and reflected waves.

9. A method for determining unknown structure of a solid, said method comprising the steps of:
- radiating first incident waves to a solid having unknown structure to thereby obtain first scattering waves;
- radiating second incident waves to said solid in the direction opposite to the direction in which said first scattering waves had travelled, to thereby obtain second scattering waves; and
- measuring the intensity of said second scattering waves and the direction in which said second scattering waves had travelled.

10. A method in accordance with claim 9 wherein said second incident waves have the same wavelength as that of said first scattering waves.

11. A method in accordance with claim 9 wherein both said first and second incident waves are monochrome waves.

12. A method for determining unknown structure of a solid, said method comprising the steps of:
- radiating first incident waves to a solid having unknown structure to thereby obtain first scattering waves;
- radiating second incident waves to said solid in the direction opposite to the direction in which said first scattering waves had travelled, to thereby obtain second scattering waves;
- measuring the intensity of said second scattering waves and the direction in which said second scattering waves had travelled; and
- solving a group of equations having a function of location of atoms as an issue of minimization in the 3n-dimensional functional space, said group of equations being constituted of the data represented by said second scattering waves.

* * * * *